United States Patent [19]

Steinhaus et al.

[11] Patent Number: 5,215,098

[45] Date of Patent: Jun. 1, 1993

[54] DATA COMPRESSION OF CARDIAC ELECTRICAL SIGNALS USING SCANNING CORRELATION AND TEMPORAL DATA COMPRESSION

[75] Inventors: Bruce M. Steinhaus, Parker; Randy T. Wells, Littleton, both of Colo.

[73] Assignee: Telectronics Pacing Systems, Inc., Englewood, Colo.

[21] Appl. No.: 744,466

[22] Filed: Aug. 12, 1991

[51] Int. Cl.$^5$ ............................................. A61B 5/0468
[52] U.S. Cl. ...................................... 128/702; 128/696
[58] Field of Search ................................. 128/696, 702

[56] References Cited

U.S. PATENT DOCUMENTS

| | | | |
|---|---|---|---|
| 4,170,992 | 10/1979 | Dillman | 128/702 |
| 4,202,340 | 5/1980 | Langer et al. | 128/419 D |
| 4,567,883 | 2/1986 | Langer et al. | 128/696 |
| 4,716,903 | 1/1988 | Hansen et al. | 128/419 PG |
| 4,721,114 | 1/1988 | DuFault et al. | 128/696 |
| 4,732,158 | 3/1988 | Sadeh | 128/702 |

OTHER PUBLICATIONS

D. Lin et al., "Identification of Ventricular Tachycardia Using Intracavitary Ventricular Electrograms: Analysis of Time and Frequency Domain Patterns", PACE, vol. 11, pp. 1592–1606 (1988).

B. M. Steinhaus et al., "Detection of Ventricular Tachycardia Using Scanning Correlation Analysis", PACE, vol. 13, pp. 1930–1936. (Dec. 1990, Part II).

Primary Examiner—Kyle L. Howell
Assistant Examiner—Scott M. Getzow
Attorney, Agent, or Firm—Gottlieb, Rackman & Reisman

[57] ABSTRACT

A method and apparatus for storing a representation of a cardiac signal by compressing the data using scan correlation and temporal data compression techniques. The method and apparatus sense cardiac signals when the heart is functioning in a known cardiac state, then characterize this known state by storing a temporally compressed template of time sequence samples. The method and apparatus may perform testing for multiple different cardiac states and store templates associated with each state. Subsequently when the heart is functioning in an unknown cardiac state, the method and apparatus monitor cardiac signals by temporally compressing samples and scan correlating these samples with the previously stored templates to derive correlation coefficients. These correlation coefficients are a basis for identifying and classifying cardiac signal waveforms. For waveforms which correlate highly with a particular template, analysis of the timing of the maximum correlation coefficient provides a fiducial time which designates the time relationship of waveforms within different cardiac cycles. The method and apparatus store information in the form of templates, fiducial timing markers, and waveform occurrence counts. This data provides the information necessary to subsequently reproduce a long-term signal record.

26 Claims, 6 Drawing Sheets

TEMPLATE — NSR (1000Hz)

FIG. 5A.

NSR (1000Hz)

IEGM

NSR (1000Hz)

TEMPLATE — NSR (50Hz)

FIG. 5D.

IEGM, NSR (50Hz)

$R^2$, NSR (50Hz)

DATA COMPRESSION OF CARDIAC ELECTRICAL SIGNALS USING SCANNING CORRELATION AND TEMPORAL DATA COMPRESSION

TECHNICAL FIELD

This invention relates generally to the storage of cardiac electrical signal data in cardiac control and monitoring devices, and more particularly to data storage systems within such devices which perform signal processing and analysis in a manner which reduces the number of individual computations required and thereby reduces energy requirements.

BACKGROUND OF THE INVENTION

A cardiac control or monitoring device processes cardiac electrical signals for numerous purposes. For example, a pacemaker may analyze one type of cardiac electrical signal, an intracardiac electrogram (IEGM), for controlling its mode of operation. Implantable cardiac devices may telemeter intracardiac electrograms for diagnostic purposes. Such devices may also store data representative of intracardiac electrogram signals in a memory within the implanted device for subsequent analysis and/or for later transmission via telemetry. Likewise, an external cardiac monitoring device may store data representing cardiac electrical signals after sensing of such signals from sensors affixed to the surface of the body or after receiving telemetered cardiac signal data which is transmitted by an implanted device. One problem with the storage of cardiac electrical signal data in either implanted or external devices is that the memory capacity of such devices is limited.

It is a goal of the present invention to provide for the storage of cardiac electrical signal data in a compressed form, thereby reducing the memory requirements of a cardiac control or monitoring device.

One method of reducing data storage requirements in a cardiac pacemaker which senses cardiac electrical signals is disclosed by Langer et al. in U.S. Pat. No. 4,567,883, entitled "Data Compression of ECG Data Using Delta Modulation", issued Feb. 4, 1986. The Langer et al. invention provides for more efficient utilization of storage memory by performing delta modulation data compression on sensed electrocardiogram data. More specifically, this delta modulation technique is termed a continuously variable slope delta modulator technique which was previously employed in voice transmission technology. This method reduces memory storage requirements by a factor of three or four (at a data rate of 200 bits per second).

Although this reduction in storage requirements is helpful, the massive volume of cardiac signal data for long-term recording which is necessary for detecting changes in cardiac function makes further reductions desirable.

Further reductions in data storage requirements are possible using the technique disclosed by Hansen et al. in U.S. Pat. No. 4,716,903, entitled "Storage in a Pacemaker Memory", issued Jan. 5, 1988. Instead of storing a representation of single amplitude or amplitude changes in regular time increment, this technique involves the storage of a time interval which has elapsed in which an input changes by a threshold amount. Further improvements are made possible by the present invention.

A knowledge of the nature of cardiac electrical signals is fundamental to an understanding of the present invention. Cardiac electrical signals are highly periodic in nature. Even patients with diseased hearts will display cardiac signal waveforms which are virtually identical for a vast majority of cardiac cycles. Furthermore, when the heart is functioning in an abnormal state in which the cardiac electrical signal waveform is different from a normal state, the abnormal waveforms will often take a second form, or other standard abnormal form, which is essentially identical from cycle to cycle. Accordingly, it is not necessary to store each sample of the cardiac electrical signal waveform to restore all the information contained in the signal. If an apparatus can identify and classify a signal for a particular cardiac cycle, it can completely restore a cardiac signal by storing only representative copies of the waveform associated with particular exemplary cardiac rhythms, together with information concerning the rate and order in which the representative waveforms occur.

One technique for identifying and classifying cardiac signal waveforms is to correlate an input signal with a standard waveform representative of a known cardiac rhythm. Correlation is the summation of the products of point-by-point multiplications of two sequences for the purpose of deriving a standard of similarity between the two waveforms. Unfortunately, correlation analysis requires such computational complexity that it is impractical in an implanted device. Because the device expends energy on each computational step and correlation requires so many computations, the lifetime of an implanted device performing correlation would be unreasonably short or the battery size too large for practical usage.

It is known that correlation analysis of intracavitary ventricular electrograms is a viable technique for analyzing cardiac waveform morphology, and that it improves specificity of cardiac rhythm recognition. For example, correlation waveform analysis is a reliable technique for discriminating ventricular tachycardia from sinus rhythm. It has been used for over two decades in the analysis of surface lead morphology as well as for analyzing esophageal electrograms, intra-ventricular electrograms and intra-atrial electrograms. While correlation analysis is effective, it requires a waveform sampling rate of about 1 kHz to properly distinguish arrhythmia waveforms. Furthermore, the number of computations it requires is too demanding for usage in the low energy environment of an implantable device.

One modified technique for performing standard correlation is by multiplying the waveform sequences in a section-by-section manner, called piecewise correlation analysis, which provides for a reduction in the number of required computations by limiting the correlation procedure to operate only in the vicinity of the R-wave. In one example of piecewise correlation, a signal processing system defines a representative "normal" signal by measuring a ventricular electrogram signal template when the heart is functioning with a normal sinus rhythm. The system specifies this template by "windowing" the waveform, detecting the QRS complex of the cardiac signal and storing a predetermined number of samples before and after the QRS complex. For example, a waveform window may include 64 samples, which contain the QRS complex and are acquired at a 1000 Hz rate. The system averages a number of these waveform windows for a preset number of cardiac cycles with the QRS complex for each cardiac cycle occurring at the same sample location within the window. After sampling and storing the template waveform, the system samples the ventricular electrogram at the same rate and for the same number of samples as was done when acquiring the template samples. The system correlates these samples with the average sinus rhythm template on a beat-by-beat basis.

To provide accurate analysis of cardiac rhythms, the piecewise correlation technique requires that the QRS complexes of the template and the sample electrogram are aligned. In piecewise correlation analysis, accurate template alignment is very important to successfully distinguish various cardiac rhythms, such as ventricular tachycardia from normal sinus rhythm or atrial fibrillation. In practice, alignment errors greater than four to five milliseconds cause a large and unpredictable variability in correlator results. Furthermore, alignment errors frequently are not recognized since a sensing determination aligned on some feature other than the R-wave may still result in a high correlation output.

Reliable template alignment is not a simple procedure. For example, a system which aligns R-waves according to a measured point of maximum intracardiac electrogram (IEGM) amplitude or corresponding to the peak derivative of the signal does not provide adequate alignment due to the large variability in amplitude and slope of the signal waveform. Signal processing of the cardiac signal to clarify the position of the R-wave using a variety of search windows and filtering techniques is helpful for particular signal morphologies but no single alignment procedure is adequate for all patients. The wide variability in cardiac signal morphologies for different patients and also for different times for the same patient cause these alignment difficulties.

Furthermore, a system which performs window alignment based on the peak cardiac signal amplitude is susceptible to errors from T-wave sensing. Occasional patients may display T-waves which are consistently larger in amplitude than R-waves. Consequently, windows may align on the T-wave or may align on the R- and T-waves in alternating cardiac cycles. Systems which align the template and sample signals based on the location of the sensed peak derivative commonly err from five to ten milliseconds because of the noisy nature of derivative signals. When combined with low pass filtering, alignment by peak derivative sensing improves somewhat but remains unacceptable.

The small size of the piecewise correlation window which is necessary to provide the computational efficiency for an implantable device leads to an additional source of alignment error. As the device performs piecewise correlation over a single cardiac cycle it may detect multiple peaks, possibly caused by T-wave sensing or detection of multiple peaks associated with the R-wave.

Full scanning correlation, in which a continuously sampled cardiac signal is correlated with a template sequence having a predetermined length smaller than the duration of the shortest possible cardiac cycle, avoids the alignment problems inherent in piecewise correlation. Unfortunately, full scanning correlation requires an excessive number of computations, and therefore too much power drain, for an implantable device.

It is, therefore, a primary object of the present invention to reduce the data storage and transmission requirements of a diagnostic test device.

It is a further object of the present invention to reduce computational and energy requirements of the a diagnostic test device by compressing cardiac electrical signal data prior to processing and storing the data.

Further objects and advantages of this invention will become apparent as the following description proceeds.

SUMMARY OF THE INVENTION

Briefly stated, and in accordance with one aspect to the present invention, a method and apparatus are provided for compressing and storing cardiac electric signals which are sensed from a patient's heart. The method and apparatus sense cardiac signals when the heart is functioning in a known cardiac state, then characterize this known state by storing a temporally compressed template of time sequence samples. The method and apparatus may perform testing for multiple different cardiac states and store templates associated with each state. Subsequently, when the heart is functioning in an unknown cardiac state, the method and apparatus monitor cardiac signals by temporally compressing samples and scan correlating these samples with the previously stored templates to derive correlation coefficients. These correlation coefficients are a basis for identifying and classifying cardiac signal waveforms. For waveforms which correlate highly with a particular template, analysis of the timing of the maximum correlation coefficient provides a fiducial time which designates the time relationship of waveforms within different cardiac cycles. The method and apparatus store information in the form of templates, fiducial timing markers, and waveform occurrence counts. These data provide sufficient information for subsequently reproducing a long-term signal record.

In accordance with another aspect of the invention, during performance of temporal data compression in the foregoing method and apparatus, the number of data time samples to be presented for a scan correlation is reduced by subtracting each of a predetermined number of consecutive noncompressed samples of input cardiac electrical signal from the most recently determined compressed sample. This predetermined number is the compression ratio. The method and apparatus then store each of the noncompressed samples and its associated absolute difference value from each subtracting step result and mutually compare each of the stored absolute difference values to determine the largest absolute difference. The current compressed sample is then set to the value of the stored non-compressed sample associated with the largest absolute difference.

BRIEF DESCRIPTION OF THE DRAWINGS

While the specification concludes with claims particularly pointing out and distinctly claiming subject matter regarded as the invention herein, it is believed that the present invention will be more readily understood from the following description, taken in conjunction with the accompanying drawings, in which:

FIGS. 5A, 5B, 5C, 5D, 5E, and 5F are sample illustrations of signal waveforms acted upon or produced at different stages of processing by the compressed correlation processor of the present invention, in which

DETAILED DESCRIPTION

Only those parts of a cardiac control or diagnostic instrument which are necessary for an understanding of the present invention are shown in the drawings. Thus, although useable in a cardioverter/defibrillator, for example, the arrhythmia reversion mechanism of the latter is not shown.

Figure 1:
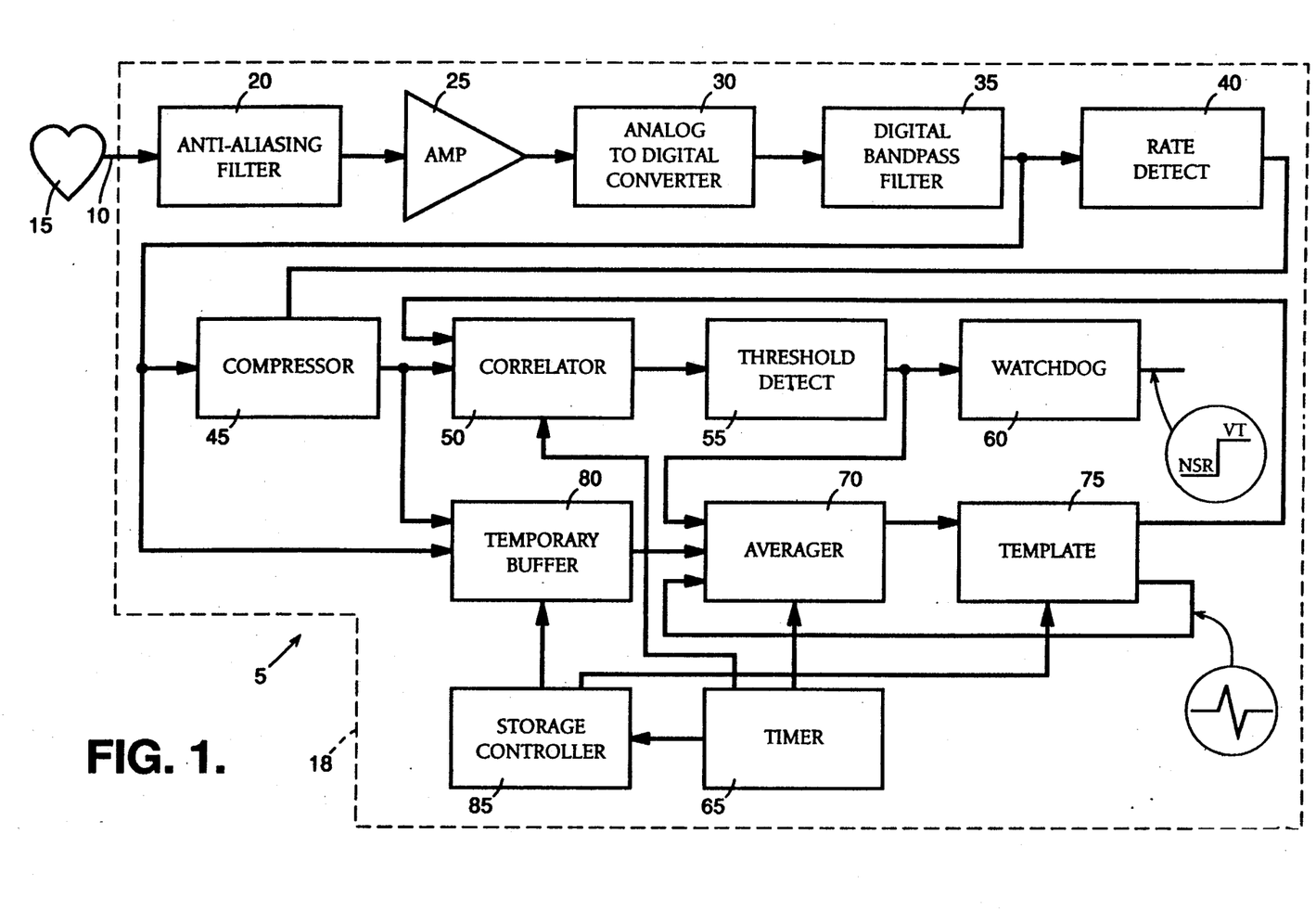
FIG. 1 is a block diagram of a preferred embodiment of the invention, in which a digital scanning correlator operates to identify and classify cardiac rhythms.

FIG. 1 illustrates a preferred embodiment of a digital correlator or scanning correlator, shown generally at 5, in accordance with the present invention. This Figure exemplifies the usage of a scanning correlator as a basic control element in a system for compressing and storing cardiac electrical signals by sampling electrocardiograms and comparing the signal with a stored signal composed of averaged normal sinus rhythm waveforms and averaged waveforms which exemplify cardiac rhythms other than normal sinus rhythm. Cardiac heartbeat signals are sensed by electrodes (not shown), which are affixed to the left ventricle of the heart 15 and electrically connected to leads 10 extending to the digital correlator electronics (not shown) contained within a case 18. The scanning correlator detects cardiac signals using one of the configurations standard in cardiac pacing: bipolar, unipolar tip-case or unipolar ring-case. Unipolar signals arise from cardiac potentials which accumulate over a large surface of the ventricle. Bipolar signals sum cardiac potentials over a smaller ventricular surface and generally contain less information than unipolar signals. A unipolar sensing configuration provides the most reliable correlation result. On the other hand, bipolar signals offer better rejection of noise, including muscle and motion artifacts, to provide the most detailed signal description of the electrophysiological state from a localized region of the ventricle.

The signal on the leads 10 is input to a low pass anti-aliasing filter 20 with a maximum high frequency cutoff of about 125 Hz. In the field of signal processing, the sampling theorem states that an analog signal, such as the signal applied to the anti-aliasing filter 20, is uniquely described by a set of uniformly spaced discrete (digital) samples taken at a particular sampling frequency, as long as no signal energy exists at frequencies greater than or equal to half this sampling frequency. The rate of half the sampling frequency is called the "folding frequency" because signals containing energy components at frequencies higher than the folding frequency, when sampled at the sampling frequency, will contribute a noise component to a reconstructed signal at the sampling frequency less the signal frequency. This noise is called aliasing noise. The high frequency cutoff (125 Hz) of the anti-aliasing filter is selected to correspond to a folding frequency appropriate for a sampling frequency of 250 Hz. Although the anti-aliasing filter cutoff is chosen to correspond to the folding frequency in the preferred embodiment of the invention, a cutoff frequency ranging down to 25 Hz or lower is prudent for practical filter designs.

The filtered signal passes through a unity gain amplifier 25 to an analog to digital converter 30 which digitizes the cardiac signal for sampling at 250 Hz. The correlator limits the frequency of the digitized cardiac signal using a digital bandpass filter 35 to attenuate signals below 0.25 and above 11 Hz to remove line frequency noise at 50 Hz or 60 Hz, while retaining essentially all of the diagnostic information contained in a cardiac signal. In the preferred embodiment of the invention, the high frequency cutoff is set to the apparently low frequency of about 11 Hz. One reason for limiting the sampled signal to this range is to eliminate or reduce artifacts arising from the aliasing of line frequency noise into the desired signal. Although the original signal is sampled at a frequency of 250 Hz, data compression reduces the effective frequency to 50 Hz. Therefore, the high frequency cutoff is set lower than the effective folding frequency of 25 Hz (half the effective sampling frequency). A cutoff frequency as low as 11 Hz prevents aliasing in filtering circuits having common attenuation characteristics to yield an appropriately small output at 25 Hz.

A signal correlator must perform many computations when calculating a single correlation coefficient. The service lifetime of an implantable device is inversely proportional to the amount of numerical processing it must perform. A rate detect block 40 controls whether the correlator is active at a given time. This embodiment of the invention may restrict the operation of signal averaging to take place only when the heart is functioning at a particular range of rates. For example, if an averaged signal is processed during cardiac cycles including some cycles which are characterized by ventricular tachycardia and other normal sinus rhythm cycles, the fine detail sought by performing signal averaging may be obscured. Rate detect block 40 determines the current heart rate and compares it to one or more predetermined rate limits. If the rate is within a pair of rate limit values, rate detect block 40 directs the averaging of the acquired signal by assigning the acquired signal to add to a particular averaging memory buffer. The device may include multiple averaging memories, although for simplification, the invention is described to include only a single averaging memory. If a device includes multiple averaging memories, the predetermined rate limits may also specify lower and upper rate limits, beyond which no signal averaging occurs to conserve energy in an implantable device.

Periodically (about once per day), the digital correlator should update the correlation template. While updating the correlation template, the rate detect block 40 controls the operations of the correlator in a different manner as compared to the operations during scanning correlation. During template updating, the rate detect block 40 prevents contamination of the template waveform with nonstandard cardiac rhythms by disabling the correlator when the cardiac rate is high. Only if the rate is characteristic of normal sinus rhythm does the rate detect block enable the correlator to update the normal sinus rhythm template The 250 Hz samples of digitized cardiac signal pass from the bandpass filter 35 to a temporal data compressor 45, and selectively to a temporary buffer 80 if the latter is enabled by a storage controller 85. Scanning correlation processing requires a number of computations, which number is approximately proportional to the square of the sample rate for both the input data and the correlation template, motivating a reduction in effective sampling rate as much as possible. The amount of possible reduction in effective sampling rate depends on the highest frequency content of the signal. For cardiac waveforms using the described compression method, compression to 50 Hz produces an accurate signal for analysis and storage. The temporal data compressor eliminates four of every five samples, saving from each group of five samples only the sample with the maximum excursion from the last saved sample, to decimate (reduce) the signal from a frequency of 250 Hz to 50 Hz.

The data compression procedure of block 45 analyzes a predetermined number of input samples to find the value of the sample having the maximum excursion, positive or negative, from the most recent output sample. The predetermined number of input samples for each output sample is the compression ratio. The output has a uniform sample period because a fixed number of input samples are evaluated for each of the output samples.

Figure 2:
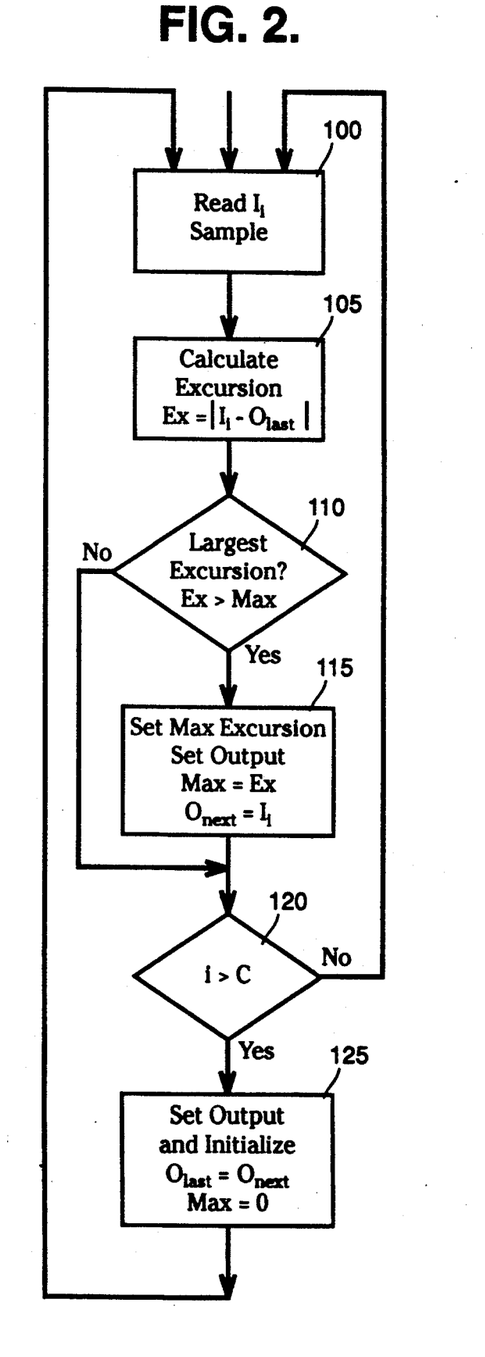
FIG. 2 is a flow chart illustrating the operational steps for one example of the data compression procedure.

FIG. 2 illustrates one embodiment of the data compression procedure. In block 100, the compressor reads the input data sample, $I_i$, beginning with the first sample ($i=1$). In block 105, the compressor calculates the excursion, Ex, from the output data sample from the last iteration of the procedure, $O_{last}$, according to the equation (1) below:

$$Ex = |I_i - O_{last}|. \qquad (1)$$

If the excursion, Ex, is greater than the maximum excursion, Max, in block 110, then the compressor (in block 115) sets the value of Max to Ex and temporarily stores the input sample, $I_i$, in a memory location for the next output data sample, $O_{next}$. Following this, or if the excursion Ex is less than the maximum excursion Max in block 110, the procedure returns via block 120 to block 100 to perform blocks 100 to 115 in a loop C times, where C is the compression ratio. After looping C times, as controlled by logic block 120, the compressor returns the result, $O_{next}$, to the calling procedure and sets the value of $O_{last}$ to $O_{next}$ to prepare for compression of the next sample in block 125.

Figure 3:
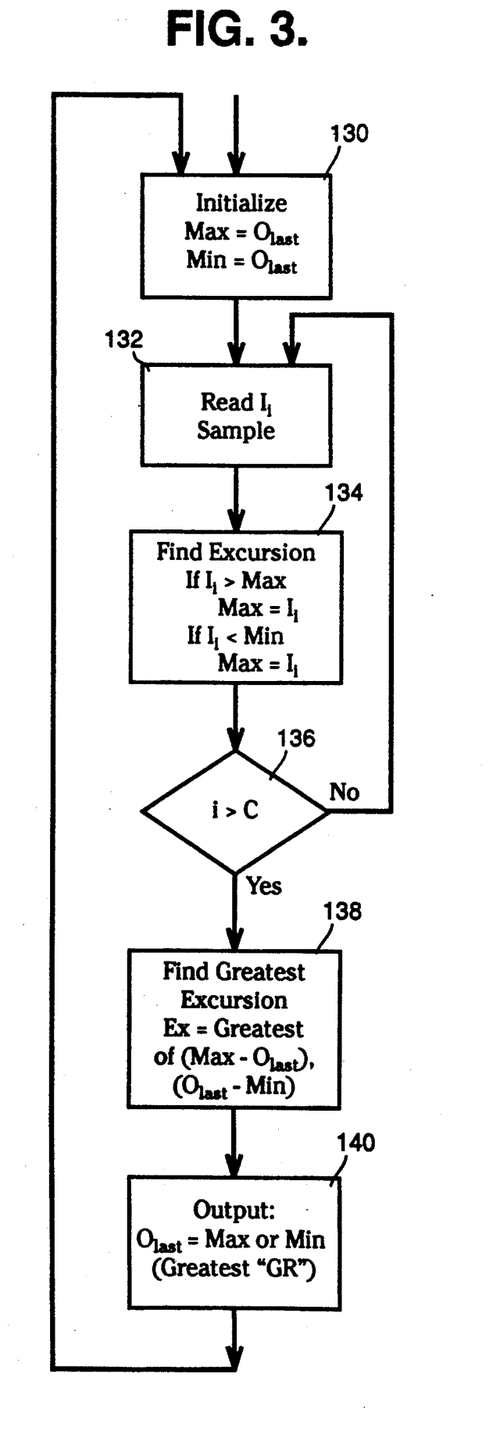
FIG. 3 is a flow chart illustrating the operational steps for a second example of the data compression procedure.

FIG. 3 illustrates a second embodiment of the data compression procedure which is more efficient in conserving the number of computing steps for some microprocessors or controllers because it avoids the absolute value determination and subtraction within its searching loop. In block 130, the compressor sets both the maximum sample, Max, and the minimum sample, Min, to the value of the output data sample from the last iteration of the procedure, $O_{last}$. The procedure enters the test loop beginning in block 132. The procedure performs blocks 132 to 136 within the loop C times as controlled by the logic test in block 136, where C is the compression ratio. Within the loop in block 132, the compressor accesses the input data sample, $I_i$, beginning with the first sample ($i=1$). In block 134, the procedure updates the maximum and minimum sample values by comparing $I_i$ to Max and Min. For a given sample I at time i, if Max is less than $I_i$, it is set to $I_i$. If Min is greater than $I_i$, it is set to $I_i$. After looping C times, in block 138 the compressor determines the positive and negative excursions, respectively, by subtracting $O_{last}$ from Max and by subtracting Min from $O_{last}$. The compressor stores the greater of the positive and negative excursions in $O_{last}$ to prepare for compression of the next sample and returns this value as the compressor result to the calling procedure in block 140.

Data compression to 50 samples per second (20 msec sample period) using this procedure preserves the majority of the information content of intracardiac electrogram data. Data compression to 25 samples per second or less results in visual degradation of the signal including the loss of temporal resolution less than the sampling period, temporal (phase) shift in the output data, and temporal widening of fast events such as a QRS complex.

The procedure for temporally compressing the template and cardiac signal sequences is simple and efficient, requiring few computations for each input sample, and provides for conservation of energy by reducing the total number of computational steps per cardiac cycle. Despite the reduction in data volume, this compression method maintains the accurate temporal and morphology information which is contained within the original cardiac signal.

In addition, this compression procedure permits "a priori" specification of the compression factor and, therefore, the computation requirements. The distinctive data compression scheme conserves information by preserving, respectively, uniform input and output sampling periods and the major amplitude changes in the original data during the rapid deflections of the QRS complex. The compression procedure is simple to implement, executes in real-time on most or all processors for signals with a bandwidth standard in cardiology applications, and provides for large compression ratios while preserving the fidelity of peak amplitude variations and waveform morphology in cardiac signals. By preserving peak amplitude variations within the compression period the procedure has no inherent low pass filter effect (at the expense of retaining large amplitude noise spikes).

The uniform sampling period, which is inherent in the data compressor of the present invention, is advantageous because it requires no special decoding algorithm prior to restoring the signal for processing or display.

In addition to reducing data storage and transmission requirements, the data compression operation of the present invention is important because it provides for a limitation with regard to the number of computations required when the system calculates the correlation function.

The key to reducing computations in scanned correlation is to temporally compress the template and input waveforms before performing the correlation computation. To perform a correlation computation requires TX multiplications per second where T is the number of samples in the template and X is the sample rate of the cardiac signal. The number of multiplications increases with the square of the sample rate. By compressing the template and sample cardiac signal each by a factor of 5, the necessary number of multiplications decreases by a factor of 25. The data compression technique of the present invention provides for compression ratios of 20:1, thereby dramatically reducing the number of necessary computations, while yielding results after correlation which are nearly identical to results produced by the correlation of signals which have not been compressed.

Again referring to FIG. 1, where a 5 to 1 compression ratio is utilized, the compressor output of block 45 is a 50 Hz digital signal which passes to a correlator 50 and possibly to temporary buffer 80, if the latter is enabled by storage controller 85. Temporary buffer 80 and storage controller 85 provide for the storage of compressed or noncompressed waveforms for some scanning compressed correlator applications. The correlator 50 correlates the input signal with a template segment of previously sampled and averaged normal sinus rhythm wave for data (NSR).

The standard correlation formula is shown in equation (2), below:

$$R = \frac{\sum_{i=0}^{N}(T_i - \mu_T)(X_i - \mu_X)}{\sqrt{\sum_{i=0}^{N}(T_i - \mu_T)^2 \sum_{i=0}^{N}(X_i - \mu_X)^2}} \qquad (2)$$

where R is the correlator result for each data sample, each $T_i$ is a template sample at time i, each $X_i$ is a cardiac signal sample, $\mu_T$ and $\mu_X$ are the means for the template samples T and the cardiac signal samples X, respectively, and N is the template length. Standard correlation requires a square root operation in the denominator of the equation, which although possible to accomplish, would be difficult to implement in the limited energy conditions of an implantable device. Rather than performing the square root operation, the preferred embodiment of the invention squares the numerator and denominator of the right side of the equation, eliminating the square root operation, and leaving the correlation result R in its squared form $R^2$. This squared form of R, termed the "correlation coefficient" is used as a surrogate for the standard result. By avoiding the computationally-intensive square root operation at the cost of only one additional multiplication operation (the squaring of the numerator of the right hand side of the equation), this method of analysis promotes efficiency and power conservation. Since the correlation coefficient $R^2$ is in the squared form, it always takes a positive value.

Standard correlation requires the determination of the means, $\mu_T$ and $\mu_X$, for both the template T, and cardiac signal X, samples. The preferred embodiment of the invention eliminates the correction for the mean since high pass filtering within the aforementioned bandpass filter substantially removes the DC component of the signal, forcing the mean to zero. By removing the mean correction, this technique saves N subtraction operations (where N is the template length) for each sample in the input waveform, X, and simplifies the computation for each sample. Note that this simplification is only possible when the length of the template is not too small in relationship to the cardiac cycle length. For this reason, the correlator within the preferred embodiment of the invention monitors the heart rate and does not allow template lengths shorter than about 10% of the minimum cardiac cycle length.

These two simplifications change the correlation function for calculating a new correlation coefficient, $R^2$, as shown in equation (3), below:

$$R^2 = \frac{\left(\sum_{i=0}^{N} T_i X_i\right)^2}{\sum_{i=0}^{N} T_i^2 \sum_{i=0}^{N} X_i^2}. \qquad (3)$$

Figure 4:
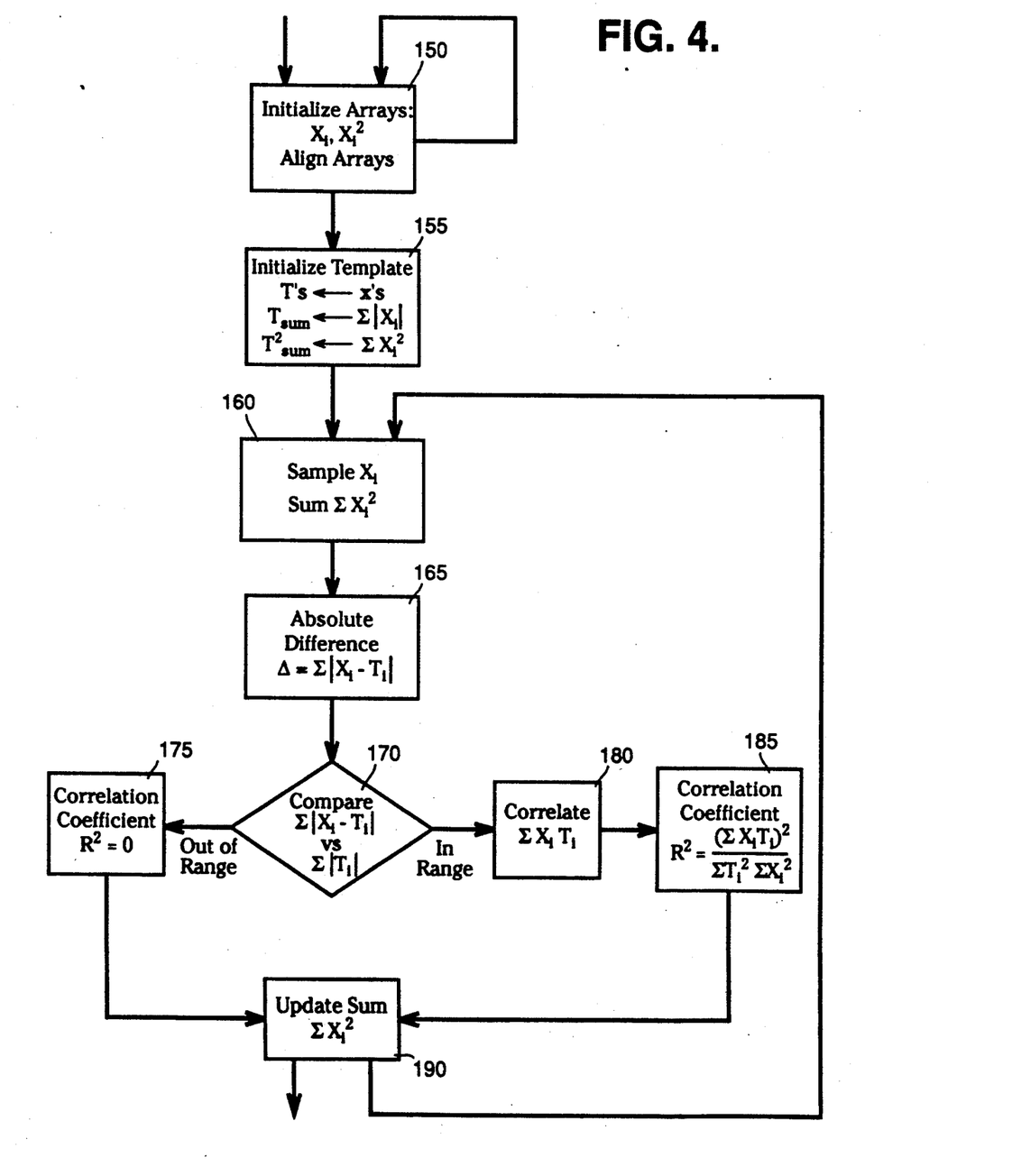
FIG. 4 is a flow chart illustrating the operational steps for the preferred embodiment of the correlator procedure.

The flowchart in FIG. 4 describes the operations performed by the correlator. Before beginning the correlation function, the correlator first initializes the cardiac signal sample arrays, $X_i$ and $X_i^2$, and the scalar value of $\Sigma X_i^2$ over the most recent N samples. In the initialization operation, each element of each array is set to zero, as is the scalar $\Sigma X_i^2$. The size of the $X_i$ and $X_i^2$ sample arrays is based on the expected number of 250 Hz samples for a sampled interval within a cardiac cycle of normal duration. For example, a common size for $X_i$ and $X_i^2$ arrays for normal sinus rhythm cardiac signals may be defined to include 80% of a typical resting heart rate escape interval, a duration of approximately 700 milliseconds. Therefore, a sample rate of 250 Hz, which is temporally compressed to 50 Hz has a compressed sample duration corresponding to each 20 millisecond interval. There are 35 compressed samples for each 700 millisecond array duration. If each sample is stored in a single eight bit byte, each array $X_i$ and $X_i^2$ is stored in 35 bytes. The size of the template arrays, $T_i$ and $T_i^2$, matches that of the arrays $X_i$ and $X_i^2$.

Block 150 is a cardiac signal sampling loop which initializes the arrays necessary for correlation processing and aligns the signal waveform within the arrays to affirm that the R-wave of the cardiac signal is within the template. In the proposed example, the alignment process establishes a 700 millisecond duration template array ending 600 milliseconds after sensing an R-wave. Within the loop, the correlator samples cardiac signal data at 250 Hz, discards four of five samples according to the data compression procedure, stores the remaining data sample in the $X_i$ array, squares the sample and stores the result in the $X_i^2$ array. Block 155 performs the second initialization step of storing the template selected in sampling block 150 in the template array, $T_i$. Block 155 also determines the sum of the elements in the array $T_i^2$ and stores the result in the scalar parameter, $\Sigma T_i^2$ for N template samples. The correlator derives these data during template formation in initialization, and maintains template validity against physiological changes over time by periodic updates.

The correlator in one embodiment of the invention establishes the template length to be 80% of the average normal sinus rhythm cardiac cycle length. Alternatively, the correlator may utilize a variable template length, which is set according to the purpose and application of the scanning correlator.

The heart beat rate varies greatly over time. Therefore, it is desirable for the template length to vary accordingly. One method of dynamically varying the template length is to truncate the template length when the heart rate interval is shorter than the stored template length. The correlator performs truncation by determining the maximum number of template array samples corresponding to the heart rate interval (the time interval for the current heart rate) measured in rate detect block 40 (of FIG. 1). The correlator will determine the correlation coefficient for no more than this maximum number, ignoring additional template samples.

The correlation coefficient, $R^2$, is normally independent of the cardiac signal amplitude because the $\Sigma X_i^2$ factors appear in both the numerator and the denominator of the correlation equation, as may be seen in equation (3) above. Therefore, it is possible that correlation of the template with noise in the cardiac signal or, more importantly, correlation of the template with random nonphysiological signals which obscure the true cardiac signal, can create an inappropriately large correlation coefficient. These random nonphysiological signals are low level signals which may correlate highly with the template due to the statistical nature of the correlation operation, but are not considered to be true physiological signals.

The correlator includes an absolute difference measurement to detect and respond to these nonphysiological signals. For each sample, $X_i$, the correlator determines the absolute value of the difference between the cardiac signal sample and the template sample. The correlator then sums the difference magnitudes for the entire sample length, N, to determine the nonphysiological signal measurement for the current cardiac cycle.

To determine the relationship of the nonphysiological signal magnitude to the signal, the correlator compares the nonphysiological signal value to a normalization parameter, $T_{norm}$. The normalization parameter is chosen to be the sum of the absolute values of the template samples for the length of the template. In computer simulation testing this averaged value of normal sinus rhythm samples has best approximated the expected signal magnitudes in the absence of nonphysiological signals. While initializing the template in block 155, the correlator determines the absolute value for each sample, $T_i$, and sums each value to create the normalization parameter, $T_{norm}$, as shown in equation (4), below:

$$T_{norm} = \sum_{i=0}^{N} |T_i|. \quad (4)$$

After initialization, control passes to block 160 which begins the cardiac signal sampling for correlation determination. To conserve energy in an implantable device, the preferred embodiment of the invention only performs the correlation function when necessary. For example, the correlation process may pause until the intrinsic cardiac rate is within a predetermined test range. The correlator may maintain all parameters and arrays while the function is inactive.

In block 160, the correlator samples the data compressed cardiac signal and stores the result in $X_i$. The correlator also updates the $X_i^2$ array and sum by squaring the cardiac signal sample and adding it to the scalar $\Sigma X_i^2$, taken from (and stored back into) a memory location.

In block 165, the correlator determines the absolute difference between corresponding template and cardiac signal samples. The absolute difference determination, shown in statement (5) below, $$\sum_{i=0}^{N} |X_i - T_1|, \quad (5)$$

takes place within a loop which sums the difference magnitudes for each corresponding sample and template pair for all the samples in the cardiac cycle.

The correlator performs the noise test in block 170 by comparing the sum of the absolute differences determined in block 165 to the normalization parameter, $T_{norm}$. If the sum of the absolute differences is too large (for example, 0.5 times the normalization parameter), the correlator determines that the system cannot determine the correlation coefficient due to the presence of excessive nonphysiological signals. In this case the correlator sets the correlation coefficient to zero in block 175. Otherwise, the correlator derives the correlation coefficient $R^2$ via blocks 180 and 185.

Assuming that the sum of the absolute differences in block 170 is within an acceptable range (i.e., the nonphysiological signal amplitude is not too large), the correlator next determines the correlation numerator product in an iterative manner for each sample in the template. Block 180 includes the correlation numerator loop calculation, wherein the correlator multiplies each element in the cardiac signal sample array, $X_i$, by the corresponding element in the previously stored template array, $T_i$, then sums these products for all N array elements.

In block 185, the correlator determines the correlation coefficient by squaring the numerator value from block 180, shown in statement (6) below, $$\left(\sum_{i=0}^{N} ((X_i)(T_i))^2\right), \quad (6)$$

and divides it by the product from block 160, shown in statement (7) below, $$\sum_{i=0}^{N} (X_i)^2, \quad (7)$$

multiplied by the product from block 155, shown in statement (8) below, $$\sum_{i=0}^{N} (T_i)^2. \quad (8)$$

In block 190, the correlator prepares for processing the next sample in block 160 by reducing the value of the memory location, shown in statement (9) below, $$\sum_{i=0}^{N} (X_i)^2, \quad (9)$$

by the value of the oldest sample in the array $X_i^2$. In this manner, the correlator reduces the number of computations by maintaining the sum during sampling, then subtracting the oldest sample from the sum and adding the newest sample for each sampling cycle.

This correlation method requires $N+34$ multiplications, 1 division and $N+5$ additions per sample, i, where N is the number of samples in the template. The device may reduce computations required to perform multiplication either by performing the correlation function in hardware, by referencing lookup tables in memory indexed by the multipliers and multiplicands or by setting the product to a minimum value if either or both the multiplier and multiplicand are too small (or negative).

The recognition of two acts allows the device to further reduce the computations for scanning correlation. First, the heart exhibits a refractory period where it is unexcitable to electrical stimuli. Secondly, the electrogram is generally a periodic waveform. A device performing operations not requiring the maximum correlator value for further processing may reduce computations by defining a refractory period following each detected heartbeat, wherein the device does not measure the correlation function. A detected heartbeat, as defined when the correlator output is greater than a predetermined threshold value, signals a time when the correlator can immediately cease operations. The duration of this inactive period may be set by external programming (in a device equipped with communication capabilities as known in the art of heart pacemakers).

The device may automatically and dynamically set the expected duration of this inactive period to a value inversely proportional to the measured heart rate or proportional to the template length. Alternatively, the device may trigger the inactive period using an external heartbeat identifier such as a hardware implemented high pass filter and threshold comparator similar to the sense inhibit which is standard in the art of cardiac pacemakers. Processing in this manner requires data storage to permit analysis of samples occurring prior to the trigger signal.

After correlating the cardiac signal with the normal sinus rhythm template in block 50 (FIG. 1), the digital correlator compares the correlation coefficient with a predetermined threshold value in block 55. The threshold is a programmed or automatically adapting threshold value.

The device includes a number of data structures in memory, each of which is associated with a particular cardiac signal morphology. These data structures include a template, upper and lower rate limits, a correlation coefficient threshold, and a correlation coefficient updating threshold. The template has a varying storage capacity, depending on the duration of the cardiac cycle associated with a particular cardiac signal morphology. The upper and lower rate limits allow the device to perform a preliminary classification of a sampled signal prior to correlation. The correlation coefficient threshold value provides a criterion for finally classifying the sampled signal after correlation. The updating threshold value assists the determination of a change in signal morphology for a particular morphology type to allow the device to track changes in morphology over time. An external controller (not shown), such as a microprocessor, may select one or more particular templates for correlation at a particular time. Thus, the data compressor may correlate a single incoming signal sequence with a number of templates for the purpose of classifying the sequence as a particular type of rhythm or morphology. For example, the digital correlator first correlates the cardiac signal with the normal sinus rhythm template in block 50 (FIG. 1), then compares the correlator result with a predetermined normal sinus rhythm threshold value in block 55.

If the correlation coefficient is smaller than the threshold value in block 55, indicating a lack of similarity between the correlator result and the template, the signal is not characteristic of normal sinus rhythm and the correlator will correlate the cardiac signal, which was stored in storage controller block 85, with one or more other stored templates. The data compressor tests the most common signal types first to promote computational efficiency. In addition, if the heart rate from rate detect block 40 is outside the predetermined rate limits for a particular template, the correlator does not perform correlation for that template.

For example, by means of programming a device may specify a particular set of cardiac rates and template morphologies which may be characteristic of ventricular tachycardia or fibrillation. A physician may define a predetermined criterion which characterizes different cardiac rhythms based on an analysis of cardiac rates, correlation coefficients characterizing one or more template morphologies, and the typical duration that these rates and correlation coefficients are sustained.

If the correlation coefficient is greater than the threshold value, demonstrating a similarity of the cardiac signal to the normal sinus rhythm template, the watchdog 60 (which may otherwise be used to notify an external controller of the occurrence of dangerous cardiac arrhythmia conditions) provides information to the external controller (not shown) which signifies the incidence of a normal sinus cardiac rhythm at this time. The external controller may log an identification code and time of occurrence for the NSR event in a data log memory (not shown).

If the correlation coefficient resulting from correlation of the cardiac signal with the normal sinus rhythm template is smaller than the NSR threshold but correlation of the cardiac signal with other stored templates yields a coefficient larger than an associated template, the watchdog 60 furnishes a code to the external controller which identifies the successful cardiac rhythm type. Again, the external controller may store the code and time information in data log memory.

After correlation-testing the cardiac signal with the normal sinus rhythm template and all stored templates for other cardiac rhythms, if no resulting correlation coefficient exceeds a predetermined associated threshold value, the watchdog 60 makes the compressed signal waveform available to the external controller for storage in data log memory.

Patient morphologies may change over time due to progression of disease. These gradual changes in morphology necessitate periodic updating of the templates to adapt each template to the new morphology and permit reliable operation of the correlator. For example, the correlator must maintain a template of normal sinus rhythm (NSR) by performing periodic template updating when the heart is functioning at normal heart rates to insure that the NSR template does not adapt to ventricular tachycardia. The timer 65 may activate the correlation procedure on the order of once per day (a reasonable interval, considering the balance between normal signal variability and power consumption requirements). The heart must be beating with an appropriate rate for the device to allow template updating. For example, the timer 65 will activate the correlation procedure only in the presence of normal sinus rate activity to maintain the normal sinus rhythm template. When the rate detector 40 indicates that the heart is functioning at a normal sinus rhythm, the device periodically (timed by timer 65) updates an averaged normal sinus rhythm waveform, by detecting R-waves of consecutive cardiac cycles and determining the cardiac rate from the interval between the R-waves in rate detect block 40. After determining the current heart rate, the device then correlates the segments of cardiac signals in block 50, and accumulates and averages selected segments for a predefined number of cardiac cycles in block 70. The digital correlator updates the averages only if the correlation coefficient exceeds the appropriate threshold (for example, 0.95) for the normal sinus heart rhythm as determined by rate detect block 40.

When the averager 70 has accumulated data for the desired number of cycles, control passes to block 75 where the digital correlator stores the template by storing the averaged current $X_i$ array into the $T_i$ array and storing the scalar $\Sigma X_i^2$ value into the scalar $\Sigma T_i^2$ memory location. The number of samples in the template segment depends on the natural sinus rate and the duration of its associated cardiac interval. The template length is preset to a percentage (from 10% to 80%) of the average cardiac interval. The correlator performs cardiac signal sampling to determine the template in a manner such that each template includes the R-wave and as much of the T-wave following the R-wave as possible, since the device predicts when the next R-wave will occur from an average of cardiac intervals of recently occurring cycles and begins sampling prior to the predicted R-wave time. If an R-wave does not occur within the sampling time or if the correlation coefficient of a given sample does not meet a threshold criterion (for example 0.9), the device does not update the accumulated average.

Figure 5A:
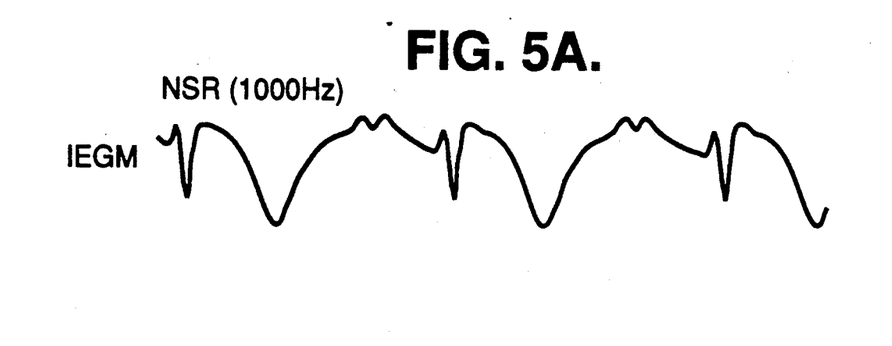
FIG. 5A is a 1000 Hz normal sinus rhythm cardiac signal.
Figure 5B:
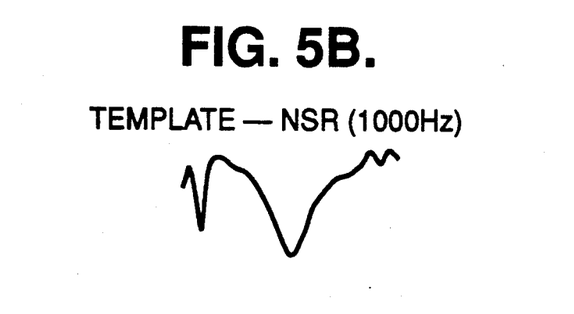
FIG. 5B is a 1000 Hz normal sinus rhythm template.
Figure 5C:
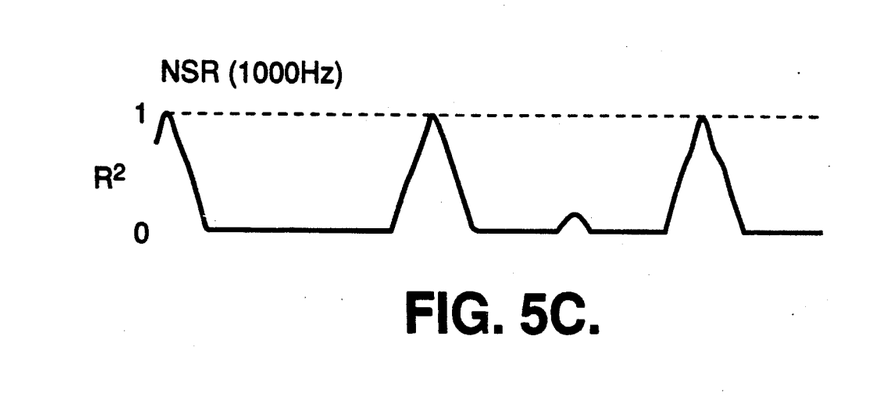
FIG. 5C is a 1000 Hz correlation result.
Figure 5D:
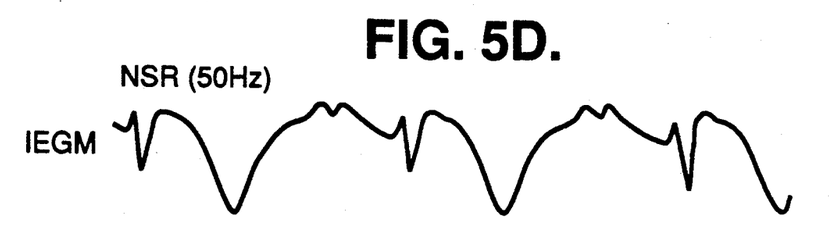
FIG. 5D is a compressed 50 Hz normal sinus rhythm cardiac signal.
Figure 5E:
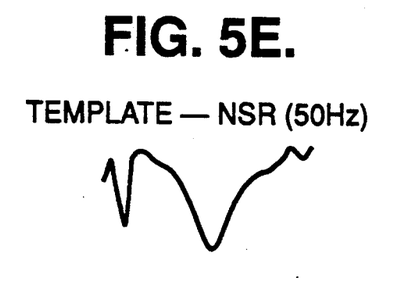
FIG. 5E is a compressed 50 Hz normal sinus rhythm template.
Figure 5F:
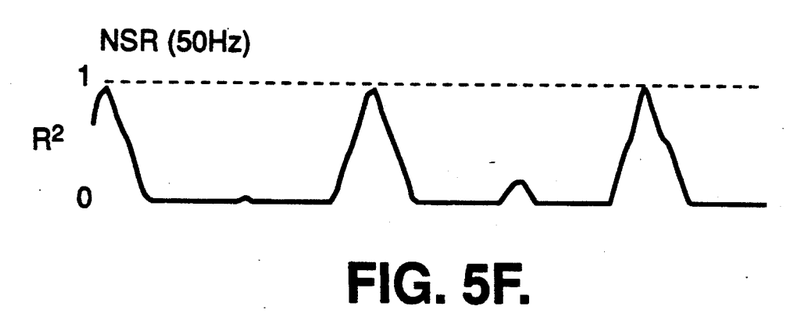
FIG. 5F is a compressed 50 Hz correlation result.

FIGS. 5A through 5F illustrate comparisons of the results obtained by correlating cardiac signals when a cardiac electrogram and a template are not data compressed (FIGS. 5A through 5C), and when the electrogram and template are data compressed (FIGS. 5D through 5F). These comparisons are accomplished by sampling actual cardiac signal samples and performing a computer simulation of the correlation procedure. When the electrogram and template are data compressed, there is a considerable savings in the computational burden. This is afforded by the procedure of compressing the data prior to correlation using the data compression scheme of the present invention. This savings in computational burden is accomplished at the cost of only a slight degradation in the correlation coefficient.

The scanning correlation coefficient of FIG. 5C is produced by correlating a normal sinus rhythm signal (FIG. 5A) with a normal sinus rhythm template (FIG. 5B), both of which are sampled at a data rate of 1000 samples per second. The correlation procedure may be visualized by sliding the template waveform of FIG. 5B along the cardiac signal waveform of FIG. 5A. The correlation coefficient of FIG. 5C is at its maximum value at each position of the template in which the morphologies of the template waveform and the cardiac signal most closely match.

Data compression of the same cardiac signal and the identical template at a 20:1 ratio reduces the effective sampling rate to 50 samples per second. Subsequent correlation of the compressed normal sinus rhythm signal (FIG. 5D) with the compressed sinus rhythm template (FIG. 5E), yields the scanning correlation coefficient of FIG. 5F. Analysis of the compressed cardiac signal waveform of FIG. 5D indicates that the compressed data retains most of the signal morphology information contained within the original data, although there is some loss of low amplitude signal information and a small degree of temporal distortion, particularly in the vicinity of the QRS complex when fast signal changes occur. The readily apparent similarity between the noncompressed and compressed correlation coefficient waveforms (FIGS. 5C and 5F, respectively) illustrates the usefulness of compressed scanning correlation, considering the large savings in data storage requirements (a twenty times reduction) and computational burden (a 400 times reduction).

Figure 6:
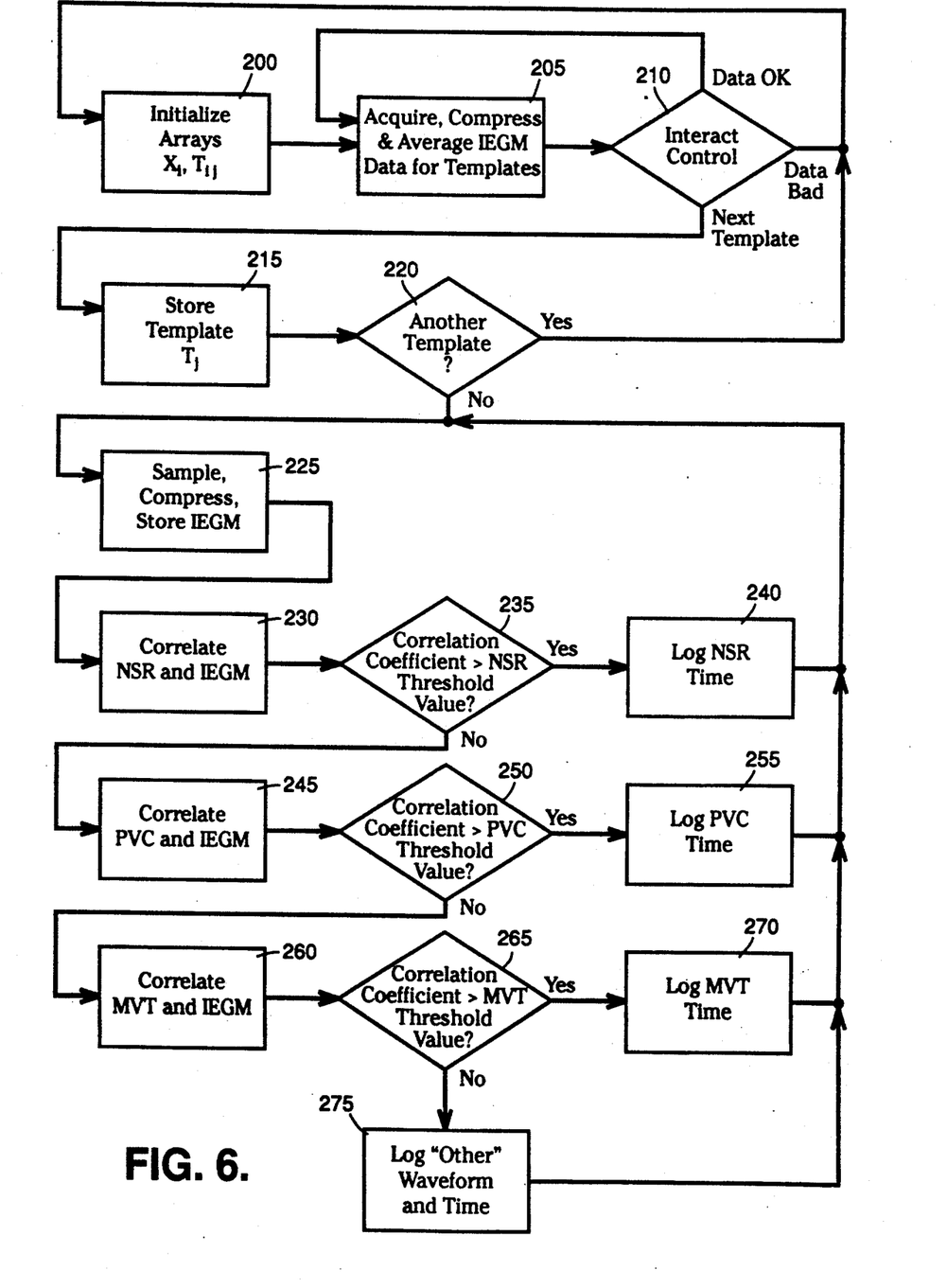
FIG. 6 is a flow diagram illustrating a procedure for performing data reduction using a scanning correlation technique.

The flow diagram of FIG. 6 illustrates the procedure for performing data reduction using the scanning correlation technique. The data reduction procedure begins with initialization of data structures in block 200 which sets each element $T_{ij}$ of one or more template arrays to zero. In the designation "$T_{ij}$", subscript "i" identifies the time sample number in the array and subscript "j" identifies a particular template array. Each template array contains a waveform representing a particular type of cardiac rhythm such as normal sinus rhythm, tachycardia or fibrillation. In block 205, the digital correlator acquires and averages intracardiac electrogram (IEGM) data for the purpose of creating templates for one or more signal morphologies. Block 205 performs data compression according to the manner of the compressor block 45 of FIG. 1 and performs correlation in the manner of correlator block 50 of FIG. 1.

Again referring to FIG. 6, template selection and storage (blocks 205 and 215) normally requires interactive input from a health practitioner to correlate each template with a type of cardiac signal morphology. Communication and telemetry functions, as are well known in the art of cardiac pacemakers, permit this interaction. Normally, a physician will first allow the digital correlator to operate in an accumulating and averaging mode to create a normal sinus rhythm (NSR) template. While the template is accumulating waveform data, the device transmits the sampled intracardiac electrograms to a display device (not shown) which the physician monitors (also in block 205). If a waveform morphology other than NSR occurs, the physician can interact with the device to restart data accumulation and averaging operations in block 200, under control mediated through logic block 210. If the physician does not request termination, control passes to block 205 for more NSR averaging. When the physician determines that enough NSR waveforms have been averaged and terminates data collection through a telemetric command to the device, control passes to logic block 215 which stores the template $T_{i1}$ for each element i of array j=1. Here, array j=1 refers to the NSR template. The physician also can interact with the device to control logic block 220 to determine whether to collect and store templates for an additional signal morphology. If so, control passes to block 200 which initializes each element $T_{i2}$ for a new template array (j=2). The procedure may loop through initialization steps 200 to 220 in this manner to set templates for multiple template arrays. For example, a particular embodiment of the invention may collect templates representing the signal morphology of preventricular contractions (PVC), monomorphic ventricular tachycardias (MVT) and other cardiac signal morphologies. The preferred embodiment of the invention collects three templates to detect NSR, PVC and MVT morphologies.

For initialization passes subsequent to the NSR (first pass, j=1) acquisition, the accumulating and averaging block 205 performs compressed scanning correlation of the accumulating waveform with the previously determined NSR template to distinguish incoming data from NSR. If the incoming signal correlates well with NSR, for example if the correlation coefficient $R^2$ is greater than a predetermined value such as 0.80, then step 205 does not update the averaged data with the currently acquired sequence. During passes subsequent to NSR template acquisition, the physician may force the heart to act with a specific morphology by physical or chemical means. These physical or chemical means are will known in the art of cardiology and electrophysiology testing and include exercise or stress testing or the application of drugs which affect cardiac performance. As in the performance of the first loop, the physician may initialize a particular template and restart sampling if data collection in block 205 is updated with an undesired waveform. In a similar manner, the third and subsequent passes may include correlation with all prior stored templates to avoid updating a new template with waveforms having a previously set morphology.

After the initialization loop of blocks 200 through 220, signal monitoring begins with block 225 which samples, data compresses and stores the intracardiac electrogram according to the method previously described in the discussion of blocks 20, 25, 30, 35, 40, 45, 80 and 85 of FIG. 1. Again referring to FIG. 6, block 230 next correlates the intracardiac electrogram waveform with the compressed NSR template, performed according to the procedure of block 50 of FIG. 1, and tests the correlation result with a predetermined threshold value, as in block 55 of FIG. 1. In FIG. 6, if the correlation result is greater than the threshold, logic block 235 directs control to block 240 which stores a short code in storage memory which identifies the fiducial time of the NSR detection. From block 240, the procedure loops back to block 225 to resume data acquisition of the waveform for additional cardiac cycles.

If the NSR correlation result is less than the threshold, logic block 235 passes procedure execution to block 245 which, assuming other signal morphology templates were set, correlates the compressed intracardiac waveform with another template (for example, the PVC template). Blocks 245 to 255 function in the same manner as blocks 230 to 240 to correlate the incoming data with a template, test the correlation result with a threshold value, store a code in memory to designate the fiducial time and morphology type.

FIG. 6 includes another set of blocks, 260 to 270, which perform the same operations as block triads, 230 to 240 and 245 to 255, but which correlate the incoming data with the MVT template. Another embodiment of the invention may correlate the data with more or fewer templates according to the wishes of the physician and the condition of the patient.

If a particular sampled waveform does not correlate with one of the stored templates as determined by logic blocks 235, 250 and 265, the signal morphology of the tested cardiac waveform is unknown. In this case, block 275 stores the entire compressed waveform in a memory array $U_{ik}$ (not shown), wherein the k array descriptor enumerates the number of acquired unknown waveforms. Block 275 also stores the time of the occurrence in a memory array $V_k$ (not shown).

After performing any of blocks 240, 255, 270 or 275, the procedure loops back to block 225 to resume data acquisition of the waveform for additional cardiac cycles.

The scanning compressed correlation method of this invention is optimized for computational efficiency and is an accurate and reliable method for distinguishing normal sinus rhythm from ventricular arrhythmias. The combination of data compression and full scanning correlation provides a reliable detector of ventricular tachycardia which is easily implemented in an antitachycardia device. A data compression procedure is normally utilized to reduce data storage requirements of an apparatus. In the present invention, the purpose of data compression is to reduce computational requirements and conserve the energy expenditure of an implantable device to more efficiently use the limited battery life.

The primary motivation for providing a computationally efficient correlation procedure and apparatus is to reduce data storage capacity requirements. A diagnostic cardiac instrument records information contained within the cardiac signal for analysis by a health professional. It may telemeter the data to an external, non-implantable device for diagnostic purposes and it may store data representative of the ECG in a memory for subsequent analysis or telemetry. Because the intracardiac waveform normally varies little from cycle to cycle, even for patients with abnormal hearts, an efficient correlation analysis procedure provides a means for storing only a single copy of most waveforms and a record of the timing of each of these waveforms. This procedure reduces storage memory requirements significantly.

An implantable cardiac (Holter) monitoring device is an example of an apparatus which uses the compressed scanning correlation method of the present invention to provide for data reduction. In this device, data storage capacity is limited. Scanning correlation techniques could allow reduction ratios up to 250 and still allow restoration of a full Holter report.

A very high correlation coefficient assures high confidence that the signal waveform is nearly identical to the template. In cardiac patients, ranging from normal to even the most abnormal, the heart functions in a normal state with a normal sinus rhythm (NSR). Therefore, most ECG waveforms exemplify normal function. Thus, if the device stores a NSR template and all the times of each beat where the correlation coefficient is greater than the threshold, sufficient information is available to reproduce the complete temporal waveform. (Since the times from the correlator are only accurate to the period of the compressed data, the device may require an independent mechanism for determining these intervals.)

The device may store templates for several classes of cardiac waveforms such as normal sinus rhythm, premature ventricular contractions or monomorphic ventricular tachycardias (VT electrograms having a single morphology). The device performs the correlation of sampled cardiac signals with the template associated with the most common cardiac rhythm, normal sinus rhythm, and only correlates the signals with other templates if the NSR correlation coefficient is too small. The device stores the alignment time and an identifier for the waveform in a log. Data reduction in this manner reduces the amount of data stored and lessens data transmission time when communicating the data via telemetry.

From the foregoing discussion, it is apparent that the present invention provides a cardiac signal data compression system within a cardiac control and monitoring device which accomplishes substantial improvement in conserving data storage requirements, computational burden, and energy while providing an effective means for distinguishing normal cardiac rhythms from abnormal rhythms.

Although the invention is described with reference to a particular embodiment, it is to be understood that this embodiment is merely illustrative of the application of the principles of the invention. Numerous modifications may be made therein and other arrangements may be devised without departing from the true spirit and the scope of the invention.

We claim:

1. A method of data compressing and storing cardiac electrical signals which are sensed from a patient's heart, comprising the steps of:

sensing cardiac electrical signals when the heart is functioning in at least one known cardiac state;

characterizing each of said at least one known cardiac states in a time sequence of template samples;

temporally compressing and storing each of said time sequences of template samples;

monitoring a time sequence of cardiac electrical signal samples when the heart is functioning in an unknown cardiac state by sampling and temporally compressing said unknown cardiac state samples, scan correlating said compressed unknown cardiac state samples with at least one of said stored compressed template sample sequences to derive correlation coefficients associated with each of said temporally compressed unknown cardiac state samples and each of said temporally compressed template samples in said at least one stored temporally compressed template sample sequence, and mutually comparing said derived correlation coefficients associated with each of said unknown cardiac state samples and each of said template samples;

classifying each cf said unknown cardiac state time sequences of cardiac electrical signal samples as included or excluded from each of said known cardiac states on the basis of the results of said mutually comparing step and codifying the results of said classifying step;

determining a fiducial time for each of said unknown cardiac state sequences on the basis of the results of said mutually comparing step; and storing a record of said codifications and associated fiducial times in a memory.

2. A method according to claim 1, further comprising the step of highpass filtering said sensed cardiac electrical signals when the heart is operating in each of said at least one known cardiac states and said unknown cardiac state to substantially eliminate the mean amplitude of each of said temporally compressed template samples and said temporally compressed unknown cardiac state samples.

3. A method according to claim 2, wherein said scan correlating sub-step of said monitoring step disregards the mean amplitude of each of said temporally compressed template samples and each of said temporally compressed unknown cardiac state samples when deriving said correlation coefficient.

4. A method according to claim 3, wherein each of said temporally compressing steps comprises the substeps of:

subtracting each of a predetermined number of consecutive noncompressed samples of said sensed cardiac electrical signal from the most recently determined compressed sample, wherein said predetermined number is a compression ratio;

storing each of said noncompressed samples and its associated absolute difference value from each subtracting step result;

mutually comparing each of said stored absolute difference values to determine the largest absolute difference; and setting the current compressed sample to the value of the stored noncompressed sample associated with the largest absolute difference.

5. A method according to claim 5, wherein said step of characterizing said known cardiac state in a time sequence of template samples comprises the substeps of:

sampling a first sequence of cardiac electrical signals sensed when the heart is functioning in a known cardiac state;

storing said first sequence samples in a template memory;

sampling and storing subsequent cardiac electrical signals;

scan correlating said subsequent cardiac electrical signal samples with said template samples to derive a template correlation coefficient;

comparing said template correlation coefficient with a template threshold value;

if said template correlation coefficient is greater than said threshold value, aligning said subsequent cardiac electrical signal samples in time;

averaging said aligned subsequent cardiac electrical signal samples into said template; and repeating said sampling and storing, scan correlating, comparing, aligning, and averaging steps for a predetermined number of iterations.

6. A method according to claim 5, further comprising the steps of:

monitoring said cardiac electrical signals to determine an intrinsic heart rate and its associated intrinsic cycle length; and setting a template length limit restricting the size of the template to a predetermined percentage of said intrinsic cycle length.

7. A method in accordance with claim 5, further comprising the steps of:

locating an R wave in said sequence of cardiac electrical signals; and aligning said first sequence samples in the template memory so that the R wave sample is stored in a predetermined sample location.

8. A method according to claim 6, further comprising the steps of:

locating an R wave in said sequence of cardiac electrical signals; and aligning said first sequence samples in the template memory so that the R wave sample is stored in a predetermined sample location.

9. A method according to claim 1, wherein each of said temporally compressing steps comprises the substeps of:

determining the differences between the most recent sample of said temporally compressed time sequence and each of a predetermined number of consecutive noncompressed samples of said sensed cardiac electrical signal sequence, wherein said predetermined number is a compressions ratio;

mutually comparing said differences to identify the sample in said sensed cardiac electrical signal sequence associated with the largest difference; and setting the current compressed sample to the value of the identified sample.

10. A method according to claim 1, wherein said step of characterizing said at least one known cardiac state in a time sequence of template samples comprises the substeps of:

sampling a first sequence of cardiac electrical signals sensed when the heart is functioning in said at least one known cardiac state;

storing said first sequence samples in a template memory;

sampling and storing subsequent cardiac electrical signals;

scan correlating said subsequent cardiac electrical signal samples with said template samples to derive a template correlation coefficient;

comparing said template correlation coefficient with a template threshold value;

if said template correlation coefficient is greater than said threshold value, aligning said subsequent cardiac electrical signal samples in time;

averaging said aligned subsequent cardiac electrical signal samples into said template; and repeating said sampling and storing, scan correlating, comparing, aligning, and averaging steps for a predetermined number of iterations.

11. A method according to claim 10, further comprising the steps of:

monitoring said cardiac electrical signals to determine an intrinsic heart rate and its associated intrinsic cycle length; and setting a template length limit restricting the size of the template to a predetermined percentage of said intrinsic cycle length.

12. A method according to claim further comprising the steps of:

locating an R wave in said sequence of cardiac electrical signals; and aligning said first sequence samples in the template memory to that the R wave sample is stored in a predetermined sample location.

13. A method in accordance with claim 11, further comprising the steps of:

locating an R wave in said sequence of cardiac electrical signals; and aligning said first sequence samples in the template memory so that the R wave sample is stored in a predetermined sample location.

14. An apparatus for data compressing and storing cardiac electrical signals which are sensed from a patient's heart, comprising:

means for sensing cardiac electrical signals when the heart is functioning in at least one known cardiac state;

means for characterizing each of said at least one known cardiac states in a time sequence of template samples;

means for temporally compressing and storing each of said time sequences of template samples;

means for monitoring a time sequence of cardiac electrical signal samples when the heart is functioning in an unknown cardiac state, said monitoring means including means for sampling and temporally compressing said unknown cardiac state samples, means for scan correlating said compressed unknown cardiac state samples with at least one of said stored compressed template sample sequences to derive correlation coefficients associated with each of said temporally compressed unknown cardiac state samples and each of said temporally compressed template samples in said at least one stored temporally compressed template sample sequence, and means for mutually comparing said derived correlation coefficients associated with each of said unknown cardiac state samples and each of said template samples;

means for classifying each of said unknown cardiac state time sequences of cardiac electrical signal samples as included or excluded from each of said known cardiac states on the basis of the results of the comparison made by said mutually comparing means, said classifying means including means for codifying the results of the classification made by said classifying means;

means for determining a fiducial time for each of said unknown cardiac state sequences on the basis of the results of the comparison made by said mutually comparing means; and means for storing a record of said codifications and associated fiducial times in a memory.

15. An apparatus according to claim 14, further comprising:

means for highpass filtering said sensed cardiac electrical signals when the heart is operating in each of said known cardiac states and said unknown cardiac state to substantially eliminate the mean amplitude of each of said temporally compressed template samples and said temporally compressed unknown cardiac state samples.

16. An apparatus according to claim 15, wherein said scan correlating means of said monitoring means disregards the mean amplitude of each of said temporally compressed template samples and each of said temporally compressed unknown cardiac state samples when deriving said correlation coefficient.

17. An apparatus according to claim 16, wherein each of said temporally compressing means further comprises:

means for subtracting each of a predetermined number of consecutive noncompressed ;samples of said sensed cardiac electrical signal from the most recently determined compressed sample, wherein said predetermined number is a compression ratio;

means for storing each of said noncompressed samples and its associated absolute difference value from each subtraction result;

means for mutually comparing each of said stored absolute difference values to determine the largest absolute difference; and means for setting the current compressed sample to the value of the stored noncompressed sample associated with the largest absolute difference.

18. An apparatus according to claim 17, further comprising:

means for sampling a first sequence of cardiac electrical signals sensed when the heart is functioning in a known cardiac state;

means for storing said first sequence samples in a template memory;

means for sampling and storing subsequent cardiac electrical signals;

means for scan correlating said subsequent cardiac electrical signal samples with said template samples to derive a template correlation coefficient;

means for comparing said template correlation coefficient with a template threshold value;

means, operative when said template correlation coefficient is greater than said threshold value, for aligning said subsequent cardiac electrical signal samples in time;

means for averaging said aligned subsequent cardiac electrical signal samples into said template; and means for repeating said sampling, storing, scan correlating, comparing, aligning, and averaging means for a predetermined number of iterations.

19. An apparatus according to claim 18, further comprising:
   means for monitoring said cardiac electrical signals to determine an intrinsic heart rate and its associated intrinsic cycle length; and
   means for setting a template length limit restricting the size of the template to a predetermined percentage of said intrinsic cycle length.

20. An apparatus according to claim 19, further comprising:
   means for locating an R wave in said sequence of cardiac electrical signals; and
   means for aligning said first sequence samples in the template memory so that the R wave sample is stored in a predetermined sample location.

21. An apparatus according to claim 20, wherein said known cardiac states include ventricular tachycardia and normal sinus rhythm.

22. An apparatus according to claim 14, wherein each of said temporally compressing means further comprises:
   means for determining the differences between the most recent sample of said temporally compressed time sequence and each of a predetermined number of consecutive noncompressed samples of said sensed cardiac electrical signal sequence, wherein said predetermined number is a compression ratio;
   means for mutually comparing said differences to identify the sample in said sensed cardiac electrical signal sequence associated with the largest difference; and
   means for setting the current compressed sample to the value of the identified sample.

23. An apparatus according to claim 14, wherein said means for characterizing said known cardiac state in a time sequence of template samples further comprises:
   means for sampling a first sequence of cardiac electrical signals sensed when the heart is functioning in a known cardiac state;
   means for storing said first sequence samples in a template memory;
   means for sampling and storing subsequent cardiac electrical signals;
   means for scan correlating said subsequent cardiac electrical signal samples with said template samples to derive a template correlation coefficient;
   means for comparing said template correlation coefficient with a template threshold value;
   means, operative when said template correlation coefficient is greater than said threshold value, for aligning said subsequent cardiac electrical signal samples in time;
   means for averaging said aligned subsequent cardiac electrical signal samples into said template; and
   means for sequentially actuating said sampling, storing, scan correlating, comparing, aligning, and averaging means for a predetermined number of iterations.

24. An apparatus according to claim 23, further comprising:
   means for monitoring said cardiac electrical signals to determine an intrinsic heart rate and its associated intrinsic cycle length; and
   means for setting a template length limit restricting the size of the template to a predetermined percentage of said intrinsic cycle length.

25. An apparatus according to claim 23, further comprising:
   means for locating an R wave in said sequence of cardiac electrical signals; and
   means for aligning said first sequence samples in the template memory so that the R wave sample is stored in a predetermined sample location.

26. An apparatus according to claim 14, further comprising:
   means for locating an R wave in said sequence of cardiac electrical signals; and
   means for aligning said first sequence samples in the template memory so that the R wave sample is stored in a predetermined sample location.

* * * * *